United States Patent [19]

Shepherd, Jr. et al.

[11] Patent Number: 4,588,534
[45] Date of Patent: May 13, 1986

[54] CHEMICAL COMPOSITION

[75] Inventors: Lawrence H. Shepherd, Jr.; William J. DeWitt; Gerhard O. Kuehnhanss, all of Baton Rouge, La.

[73] Assignee: Ethyl Corporation, Richmond, Va.

[21] Appl. No.: 202,008

[22] Filed: Oct. 29, 1980

[51] Int. Cl.$^4$ .................. C07C 143/02; C09K 3/00
[52] U.S. Cl. ................ 260/513 R; 260/513 B; 252/8.55 D
[58] Field of Search ............ 260/513 B, 513 R; 252/8.55 D

[56] References Cited

U.S. PATENT DOCUMENTS

| | | | |
|---|---|---|---|
| 2,241,421 | 5/1941 | Price et al. | 260/513 R |
| 2,427,577 | 9/1947 | Smith | 260/513 R |
| 3,271,444 | 9/1966 | Percival et al. | 260/513 B |
| 3,291,822 | 12/1966 | Baumann et al. | 260/513 B |

FOREIGN PATENT DOCUMENTS 4941415 12/1970 Japan ................ 260/513 B

*Primary Examiner*—Alan Siegel
*Attorney, Agent, or Firm*—Donald L. Johnson; John F. Sieberth; Joseph D. Odenweller

[57] ABSTRACT

An ether sulfinate/sulfonate or disulfonate having the following formula:

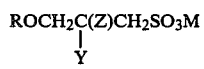

wherein:
R is a hydrocarbon group having from about 6 to about 24 carbon atoms,
Y is SO$_2$M or SO$_3$M,
Z is hydrogen or a methyl group, and
M is an alkali metal, alkylammonium or ammonium cation and mixtures of each of said sulfinate/sulfonate and said disulfonate with an ether monosulfonate having the following formula:

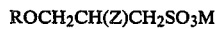

wherein:
R is a hydrocarbon group having from about 6 to about 24 carbon atoms,
Z is hydrogen or a methyl group, and
M is an alkali metal, alkylammonium or ammonium cation.

10 Claims, No Drawings

CHEMICAL COMPOSITION

BACKGROUND OF THE INVENTION

The present invention relates to new compositions of matter, suitable for use as a foaming agent and a surfactant for enhanced oil recovery use.

In general, synthetic detergents do not function well in brine solutions. Foam volume is decreased, foam stability is poor and often the active materials in the detergent are precipitated.

It has been discovered that the reaction product of sulfur dioxide and sodium hydroxide with alkyl allyl ethers produces novel compounds which have good brine solubility and good foam stability. Such products also have good foam volume and stability in cold water.

SUMMARY OF THE INVENTION

The present invention relates to new compositions of matter having the following formulas:

$$ROCH_2C(Z)CH_2SO_3M \text{ or } ROCH_2C(Z)CH_2SO_3M;$$
$$\phantom{ROCH_2C(Z)CH_2SO_3M \text{ or } R}|\phantom{OCH_2C(Z)CH_2SO_3}|$$
$$\phantom{ROCH_2C(Z)CH_2SO_3M \text{ or }}SO_2M\phantom{XXXXX}SO_3M$$

or a mixture of $$ROCH_2CH(Z)CH_2SO_3M \text{ and } ROCH_2C(Z)CH_2SO_3M;$$
$$\phantom{XXXXXXXXXXXXXXXXXXXXXXXXXXXXX}|$$
$$\phantom{XXXXXXXXXXXXXXXXXXXXXXXXXXXX}SO_2M$$

or a mixture of $$ROCH_2CH(Z)CH_2SO_3M \text{ and } ROCH_2C(Z)CH_2SO_3M;$$
$$\phantom{XXXXXXXXXXXXXXXXXXXXXXXXXXXXX}|$$
$$\phantom{XXXXXXXXXXXXXXXXXXXXXXXXXXXX}SO_3M$$

wherein R is a hydrocarbon group having from about 6 to about 24 carbon atoms. The hydrocarbon group may be either paraffinic or aromatic and includes straight chained or branched alkyl groups, alkaryl groups, arylalkyl groups and alkylarylalkyl groups. Linear alkyl groups having from 6 to 18 carbon atoms are preferred and alkyl groups of 10 to 14 carbon atoms are most preferred. Z is hydrogen or a methyl group. M is an alkali metal, alkylammonium or ammonium cation. Sodium is the preferred alkali metal.

DESCRIPTION OF THE PREFERRED EMBODIMENT

The ether sulfonate is prepared by reacting an organic compound containing a hydroxyl group such as an alcohol or phenol with an organic halide to produce an ether. The ether is then reacted with a base such as sodium hydroxide and sulfur dioxide or other suitable sulfur containing compound such as an alkali metal bisulfite, meta bisulfite or sulfite, in the presence of a suitable catalyst to produce the ether sulfonate and the corresponding sulfinate/sulfonate. The ammonium or alkylammonium salts of said sulfur compounds may also be used. Any ether sulfinates present may then be oxidized to the corresponding ether sulfonates.

The most preferred compositions of the present invention are prepared by reacting a linear primary alcohol with allyl chloride to form an alkyl allyl ether and then reacting said ether with sulfur dioxide and sodium hydroxide in the presence of a suitable catalyst to form a mixture of alkyl allyl ether sulfinates and sulfonates.

A preferred method of preparation is represented by the following equations:

$$ROH + ClCH_2CH=CH_2 + NaOH \xrightarrow{catalyst} \quad (1)$$
$$ROCH_2CH=CH_2 + H_2O + NaCl$$

$$ROCH_2CH=CH_2 + SO_2 + NaOH \xrightarrow{catalyst} \quad (2)$$
$$ROCH_2CH_2CH_2SO_3Na + ROCH_2CHCH_2SO_3Na$$
$$\phantom{XXXXXXXXXXXXXXXXXXXXXXXXXXX}|$$
$$\phantom{XXXXXXXXXXXXXXXXXXXXXXXXXX}SO_2Na$$

$$ROCH_2CH_2CH_2SO_3Na + ROCH_2CHCH_2SO_3Na + \quad (3)$$
$$\phantom{XXXXXXXXXXXXXXXXXXXXXXXXXXX}|$$
$$\phantom{XXXXXXXXXXXXXXXXXXXXXXXXXX}SO_2Na$$

$$H_2O_2 \longrightarrow$$

$$ROCH_2CH_2CH_2SO_3Na + ROCH_2CHCH_2SO_3Na$$
$$\phantom{XXXXXXXXXXXXXXXXXXXXXXXXXXX}|$$
$$\phantom{XXXXXXXXXXXXXXXXXXXXXXXXXX}SO_3Na$$

wherein R is an alkyl group having from 6 to 18 carbon atoms, with 10 through 14 carbon atoms being preferred.

In more detail, a preferred method of preparing the novel ether sulfonates involves preparing materials of the type having the formula:

$$ROCH_2C(Y)(Z)CH_2SO_3M$$

wherein R is preferably a $C_6$ to $C_{18}$ alkyl group, more preferably a $C_{10}$ to $C_{14}$ alkyl group, and most preferably a mixture of $C_{10}$ to $C_{14}$ alkyl groups, a $C_6$ to $C_{24}$ alkaryl group, a $C_6$ to $C_{24}$ arylalkyl group; Y is H, $SO_2M$ or $SO_3M$; M is alkali metal, ammonium or alkylammonium cation and preferably Na; and Z is H or $CH_3$.

In the preparation of the ether sulfonates of this invention, a hydroxy-containing compound of the formula:

ROH wherein R is as defined above, is reacted with an unsaturated organic halide having the formula:

$$XCH_2C=CH_2$$
$$\phantom{XXX}|$$
$$\phantom{XXX}Z$$

wherein X is a halide and preferably chlorine, and Z is defined as above, in the presence of a base such as sodium hydroxide and a suitable phase transfer catalyst such as tributylmethylammonium chloride to produce an ether of the formula below, sodium chloride and water:

$$ROCH_2CH=CH_2$$
$$\phantom{XXXXX}|$$
$$\phantom{XXXXX}Z$$

wherein R and Z are defined as above.

The ether is then reacted with sodium hydroxide and sulfur dioxide in an isopropyl alcohol and water solution and in the presence of a suitable catalyst such as tertiary butyl perbenzoate to produce the ether sulfonate, and the corresponding sulfinate/sulfonate.

The preferred alcohols which may be employed as reactants in preparing the ethers are those having the general formula:

ROH wherein R is a $C_6$ to $C_{18}$ radical or mixtures thereof. A most preferred alcohol composition is a mixture of 25% $C_{10}$/50% $C_{12}$/25% $C_{14}$ alcohols.

The starting hydroxy-containing compounds used to produce the ethers of the invention may be chosen from a wide variety of available compounds. Thus, for example, natural or synthetic fatty alcohols preferably containing from about 6 to 18 carbon atoms may be used and include such alcohols as hexyl, octyl, decyl, dodecyl, tetradecyl, hexadecyl, and octadecyl as well as alcohols such as lauryl, myristyl, cetyl, stearyl, and tallow, and mixtures of any of these synthetic and/or natural alcohols.

Alcohols having an odd number of carbon atoms as well as those having an even number of carbon atoms are also suitable. An example of the former are those alcohols produced by hydroformylation of even carbon numbered olefins. Combinations and/or mixtures of the various types of alcohols are also suitable.

Particularly useful alcohols here include Ziegler-type primary linear alcohols prepared from trialkylaluminum mixtures made by way of ethylene polymerization, subsequent oxidation, and hydrolysis of the resultant aluminum alkoxides as set out in U.S. Pat. No. 3,598,747 and other alcohols of this type.

Other suitable hydroxy compounds are alkyl substituted phenols and aryl alcohols. Such reactants include, for example, nonylphenol, dinonylphenol, cresol and the like. Particularly preferred are hydroxy compounds having the following structural formula:

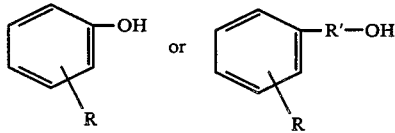

wherein R is an alkyl group containing from 1 to 18 carbon atoms, and R' is an alkylene group containing 1 to 18 carbon atoms.

Both allyl halides and methyl substituted allyl halides may be used as reactants. The term "allyl halide" as used herein includes both allyl halide and methallyl halide.

Normally, first step of the process of preparing the novel compositions of the invention involves reacting an alcohol or hydroxy compound of the type described above with an allyl halide. Preferred halides are allyl chloride, allyl bromide, methallyl chloride and methallyl bromide. This step is carried out in the presence of a strong base such as an alkali metal hydroxide and a suitable phase transfer catalyst such as tri-butylmethylammonium chloride. Preferred bases are sodium hydroxide and potassium hydroxide. The reaction proceeds best using anhydrous sodium hydroxide in pellet or flaked form. Conversions of alcohol are often as high as 95%. Only a few percent of by-product diallylether is formed.

The allyl halide and hydroxy-containing compound can be reacted on a mole per mole basis, however, an excess of allyl halide is preferred. An excess of base is normally employed; however, the amount used may range from about 0.5 molar equivalents to about 5.0 molar equivalents per molar equivalent of the hydroxy-containing compound employed.

The step involving formation of the allyl ether compound may be carried out over a wide range of process variables of time, temperature, pressure, etc. Usually, this step of the reaction is carried out at a temperature ranging from about room temperature up to about 250° C. More often the reaction temperature is 25°–200° C. and most often ranges from about 50° C. to about 150° C. The time of reaction likewise may be considerably varied from say about ¼ to about 24 hours. More often the reaction is complete in 1–10 hours. Again, the first step of the process of the invention may be run at atmospheric, superatmospheric or autogenous pressures. Thus, for example, an autoclave may be used. Usually the pressure ranges from about 5 to about 500 psig. More often the pressure is 5–100 psig.

The allyl ether produced above is then in turn reacted with sulfur dioxide and sodium hydroxide or other sources of bisulfite ion to produce the desired ether sulfonates. The ranges of time, temperature and pressure applicable to the first step of the invention are also applicable here. This step of the invention is preferably carried out in presence of an aqueous media wherein about 50 percent or more of the solvent is composed of water on a weight basis. Suitable water miscible organic solvents for such a co-solvent system include methanol, ethanol, isopropanol, and other solvents of this type.

The step of producing the sulfinate/sulfonate, etc. is typically conducted at a pH range of about 1 to 7. The pH influences the ratio of mono to disulfonate (sulfinate included) formed. At a pH of 4, the mono/di sulfonate ratio is about 40/60 but at a pH of 7 the ratio is reversed to about 60/40. Reaction is much more rapid at low pH (1 hour or less at pH 4 vs. 6 hours at pH 7), and catalyst consumption is significantly lower. Functionally, there is little difference between products rich in mono-sulfonates and those rich in di-sulfonates. Isopropyl alcohol or other co-solvent present is normally removed before the oxidation step.

The oxidation step may be carried out wherein any sulfinates are oxidized to sulfonates. This step is illustrated as follows:

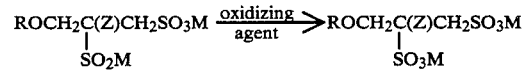

wherein R is a hydrocarbon group having from about 6 to about 24 carbon atoms. The hydrocarbon group may be either paraffinic or aromatic and includes straight chained or branched alkyl groups, alkaryl groups, arylalkyl groups and alkylarylalkyl groups. Linear alkyl groups having from 6 to 18 carbon atoms are preferred and alkyl groups of 10 to 14 carbon atoms are most preferred. Z is hydrogen or a methyl group. M is an alkali metal, alkylammonium or ammonium cation. Sodium is the preferred alkali metal.

A preferred oxidizing agent is hydrogen peroxide. Any other suitable oxidizing agent, for example chlorine, may be used.

The following examples typically illustrate the preferred process for making the novel compositions of the invention. It is understood, of course, that these examples are merely illustrative and that the invention is not to be limited thereto.

General Procedure

Step A

One mole of an appropriate alcohol (or hydroxy compound), 1.6 moles (60% excess) of allyl chloride (or halide), and 2.9 moles (190% excess) of sodium hydroxide (base) are charged to a reactor or pressure vessel equipped with an internal agitator.

One mole percent of a suitable phase transfer catalyst such as tetrabutylammonium chloride, tributylmethylammonium chloride or any other suitable catalyst is added to the mixture.

The mixture is vigorously stirred while heating to about 110° C.–120° C. for about three hours at an autogenous pressure of about 50 psig.

Reactor pressure is carefully released or vented and, while still heated, by-product diallyl ether and unreacted allyl chloride are recovered by distillation.

While still hot and before the sodium hydroxide/sodium halide (chloride) mixture solidifies, sufficient water is added to produce about a 20 percent salt solution. The product layer of alkyl allyl ether of about 95 percent purity floats on the surface and is collected.

If desired, the product can be further purified by vacuum distillation.

The foregoing procedure of Step A may be represented by the following equation:

ROH + CH$_2$=CHCH$_2$Cl + NaOH $\xrightarrow{\text{catalyst}}$

ROCH$_2$CH=CH$_2$ + NaCl

Step B

A 10% aqueous solution of sodium hydroxide containing 1.0 moles of sodium hydroxide is prepared in an alkali resistant vessel.

Sufficient sulfur dioxide is added to adjust the pH to the desired range, e.g. 0.86 moles gives a pH of about 6.8 and 2.0 moles gives a pH of about 4.0.

Isopropyl alcohol is added in an amount approximately equal to the volume of water in the solution.

One mole of the appropriate alkyl allyl ether (product of Step A) is added.

The reactor or vessel is heated to reflux under nitrogen at ~80° C.

About 0.02 moles of a suitable catalyst such as t-butyl perbenzoate is added. Any other suitable catalyst may be used.

The reaction mixture is vigorously stirred. The system is two-phase. The pH is monitored. After an induction period of about 30 minutes to one hour, a slow rise in pH is noted. As the reaction progresses sulfur dioxide is added to control the pH. The reaction is usually complete in about two to three hours.

After the reaction is complete, using atmospheric distillation, isopropyl alcohol is distilled off and recovered.

Since product composition is controlled by pH, the final pH ranges from about 3 to 7.

The foregoing procedure of Step B may be represented by the following equation:

ROCH$_2$CH=CH$_2$ + NaOH + SO$_2$ $\xrightarrow[\text{catalyst}]{\text{iPrOH}}$

ROCH$_2$CHCH$_2$SO$_3$Na
|
Y wherein Y=H and SO$_2$Na.

Under these conditions, i.e. a pH range of 4 to 7, a product containing both an alkyl ether mono-sulfonate and an alkyl ether sulfinate/sulfonate is formed.

A nitrogen blanket is preferably used to prevent any undesirable side reactions.

The product of Step B is treated with an oxidizing agent to convert any sulfinate groups to the corresponding sulfonate group as described in Step C, hereinafter.

Step C

At atmospheric pressure, the product of Step B is treated with hydrogen peroxide or other suitable oxidizing agent. If further concentration of product is desired, residual water may be removed by distillation.

The procedure may be illustrated by the following equation:

ROCH$_2$CHCH$_2$SO$_3$Na $\xrightarrow{\text{H}_2\text{O}_2}$ ROCH$_2$CHCH$_2$SO$_3$Na
|                                                        |
SO$_2$Na                                                 SO$_3$Na

EXAMPLE 1

In accordance with the foregoing procedure of Step A, an alkyl allyl ether was prepared by charging in sequence to a small autoclave the following:
158.0 grams of n-decyl alcohol
116.0 grams of crushed sodium hydroxide
122.4 grams of allyl chloride
3.14 grams of tributylmethylammonium chloride
    (75% aqueous solution).

The mixture was vigorously stirred and the reaction was maintained at 110° to 120° C. for about three hours at a pressure of 30 to 40 psig. After the reaction mixture was allowed to settle overnight, the autoclave was opened and 300 ml of hot water was added. Afterwards, the reaction mixture was discharged and the phases separated. Then the organic layer was washed with dilute hydrochloric acid and with hot water until the wash water had a neutral reaction. Subsequently, the product, decyl allyl ether, was recovered after volatiles were removed under vacuum. Vapor Phase Chromatographic (V.P.C.) analysis showed the presence of 9.9% of unreacted alcohol and 90.1% decyl allyl ether.

EXAMPLE 2

Example 1 was repeated except that after the reaction was complete and the mixture cooled to 60° to 65° C., the autoclave was opened. The solids were dissolved by the addition of 500 ml of hot water. V.P.C. analysis of the organic layer showed the presence of 12.9% unreacted alcohol and 85.0% decyl allyl ether and 2.1% other lower boiling products.

EXAMPLE 3

Another alkyl ether was prepared using the procedure described in Example 1, wherein the following were charged in sequence:
186.3 grams of n-dodecyl alcohol
116.0 grams of sodium hydroxide pellets
122.4 grams of allyl chloride
3.14 grams of tributylmethylammonium chloride
    (75% aqueous solution).

After reaction, the autoclave was allowed to cool to 60° to 65° C. and 300 ml of hot water added to the reaction mixture and agitated. The phases of the reaction mixture were separated and the organic layer washed with dilute hydrochloric acid. Analysis showed that a relatively high purity dodecyl allyl ether product was obtained.

EXAMPLE 4

Using a 5-gallon stainless steel autoclave, and following the procedures of Step A and Example 1, a mixed alkyl allyl ether was prepared by charging the following to the autoclave:
1398 grams or 30 wt. percent of decyl alcohol
1863 grams or 40 wt. percent of dodecyl alcohol
1398 grams or 30 wt. percent of tetradecyl alcohol
4659 grams total of $C_{10/12/14}OH$
2900 grams of sodium hydroxide
3060 grams of allyl chloride
78.5 grams of tributylmethylammonium chloride (75% aqueous solution), After completion of reaction under the condition of Example 1 and allowing the mixture to settle, a sample was withdrawn. The sample was analyzed by V.P.C. which indicated a purity of 95% for the mixed $C_{10}$, $C_{12}$ and $C_{14}$ alkyl allyl ethers. The crude ether was then vacuum stripped to remove traces of low boiling components.

EXAMPLE 5

In accordance with the foregoing procedure of Step B a mixture of a sulfinate/sulfonate and sulfonate is formed using the following:
5481 grams alkyl allyl ether (95% purity)
1566 grams sodium hydroxide
14.9 liters water
2270 grams sulfur dioxide
14.9 liters isopropyl alcohol
74 grams t-butyl perbenzoate (catalyst).

The sodium hydroxide (pellets) was dissolved in the water with stirring. This caustic solution was cooled and sulfur dioxide was passed through the solution until 2270 grams was absorbed, which took about one hour. This solution was then transferred to a glass-lined 13 gallon autoclave. The isopropyl alcohol, alkyl allyl ether and catalyst were added. Temperature and pH measurements were taken at intervals of 10 minutes initially, then 15 minutes and then 30 minutes until the reaction was completed. See data below. The reaction product was stripped by heating to the boiling point of isopropyl alcohol. A product consisting of 40% alkyl ether mono sulfonate and 60% alkyl ether sulfinate/sulfonate was produced.

| Time (minutes) | Temperature (C.°) | pH | Appearance Reaction Product |
| --- | --- | --- | --- |
| 0 | 43.0 | 3.90 | Two phase |
| 10 | 46.0 | 3.96 | Two phase |
| 20 | 55.0 | 4.06 | Two phase |
| 35 | 67.0 | 3.95 | Nearly homogeneous |
| 50 | 72.0 | 3.93 | Nearly homogeneous |
| 65 | 73.0 | 3.88 | Nearly homogeneous |
| 80 | 78.5 | 3.92 | Homogeneous |
| 110 | 82.5 | 3.92 | Homogeneous |
| 170 | 81.5 | 4.01 | Homogeneous |
| 200 | 80.5 | 4.01 | Homogeneous |
| 230 | 81.5 | 4.01 | Homogeneous |
| 260 | 81.5 | 4.00 | Homogeneous |

EXAMPLE 6

The product mixture of Example 5 was oxidized by treating with hydrogen peroxide. The sulfinate groups were oxidized to sulfonates and the final product consisted of a mixture of alkyl ether monosulfonates and alkyl ether 1,2-disulfonates as shown in Step C.

A foam performance comparison of an alkyl ether sulfonate of the present invention with a well-known commercial foaming agent was made.

The alkyl allyl ether sulfonate was prepared from a blend of 25% $C_{10}$, 50% $C_{12}$ and 25% $C_{14}$ linear primary alcohols.

The commercial foaming agent tested is identified by the trade name E. F. AGENT A. It is an anionic liquid foaming agent. A typical composition is as follows:

| | |
| --- | --- |
| Active Ingredient | 60 wt. % |
| Solids | 63 wt. % |
| Water | 31 wt. % |
| Alcohol | 6 wt. % |

The test consisted of preparing a solution of 0.05 or 0.1% active detergent in water of 300 ppm hardness at 5° C. and agitating the solution for one minute in a Waring blender. The contents of the blender were immediately poured into a graduated cylinder and the total volume of liquid and foam measured. After 1, 2 and 5 minutes standing at room temperature the volume of liquid drained to the bottom was measured.

The data are as follows:

| | Conc. = 0.05% | | | | Conc. = 0.10% | | | |
| --- | --- | --- | --- | --- | --- | --- | --- | --- |
| | Initial Foam, cc | Drainage Volume, cc | | | Initial Foam, cc | Drainage Volume, cc | | |
| | | 1 min. | 2 min. | 5 min. | | 1 min. | 2 min. | 5 min. |
| EFA | 255 | 9 | 20 | 60 | 470 | 1 | 3 | 16 |
| Sulfonate Mixture | 182 | 13 | 30 | 68 | 270 | 4 | 13 | 44 |

The foregoing disclosure and description of the invention is illustrative and explanatory thereof and various changes in the illustrated process may be made within the scope of the appended claims without departing from the spirit of the invention.

What is claimed is:
1. The compositions

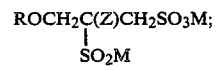

$$ROCH_2C(Z)CH_2SO_3M;$$
$$|$$
$$SO_2M$$

or

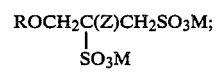

$$ROCH_2C(Z)CH_2SO_3M;$$
$$|$$
$$SO_3M$$

or a mixture of

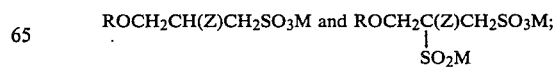

$$ROCH_2CH(Z)CH_2SO_3M \text{ and } ROCH_2C(Z)CH_2SO_3M;$$
$$|$$
$$SO_2M$$

or a mixture of $$\text{ROCH}_2\text{CH(Z)CH}_2\text{SO}_3\text{M} \text{ and } \text{ROCH}_2\underset{\underset{\text{SO}_3\text{M}}{|}}{\text{C(Z)}}\text{CH}_2\text{SO}_3\text{M};$$

wherein

R is a hydrocarbon group having from about 6 to about 24 carbon atoms,

Z is hydrogen or a methyl group,

M is an alkali metal, alkylammonium or ammonium cation.

2. An aqueous solution of any composition or combination of the compositions of claim 1.

3. The compositions of claim 1, wherein R is predominantly a linear alkyl group having from 6 to 18 carbon atoms.

4. The compositions of claim 1, wherein R is a mixture of linear alkyl groups having from 10 to 14 carbon atoms.

5. The compositions of claim 1, wherein M is sodium.

6. A composition of claim 1, wherein the composition is that defined by the formula:

$$\text{ROCH}_2\underset{\underset{\text{SO}_2\text{Na}}{|}}{\text{CH}}\text{CH}_2\text{SO}_3\text{Na}$$

wherein R is a linear alkyl group having from 6 to 18 carbon atoms.

7. A composition of claim 1, wherein the composition is that defined by the formula:

$$\text{ROCH}_2\underset{\underset{\text{SO}_3\text{Na}}{|}}{\text{CH}}\text{CH}_2\text{SO}_3\text{Na}$$

wherein R is a linear alkyl group having from 6 to 18 carbon atoms.

8. A composition of claim 1 wherein the composition is a mixture of compounds defined by the formulas:

$$\text{ROCH}_2\underset{\underset{\text{SO}_2\text{Na}}{|}}{\text{CH}}\text{CH}_2\text{SO}_3\text{Na} \text{ and } \text{ROCH}_2\text{CH}_2\text{CH}_2\text{SO}_3\text{Na}$$

or $$\text{ROCH}_2\underset{\underset{\text{SO}_3\text{Na}}{|}}{\text{CH}}\text{CH}_2\text{SO}_3\text{Na} \text{ and } \text{ROCH}_2\text{CH}_2\text{CH}_2\text{SO}_3\text{Na}$$

wherein R is a linear alkyl group having from 6 to 18 carbon atoms.

9. The composition of claim 1, wherein the composition is a mixture of the following compounds:

$$\text{C}_{10-14}\text{H}_{21-29}\text{OCH}_2\text{CH}_2\text{CH}_2\text{SO}_3\text{Na}$$

and $$\text{C}_{10-14}\text{H}_{21-29}\text{OCH}_2\underset{\underset{\text{SO}_3\text{Na}}{|}}{\text{CH}}\text{CH}_2\text{SO}_3\text{Na}$$

10. The compositions of claim 1, wherein R is an alkyl group, an aryl group, an alkylaryl group or an alkylarylalkyl group.

* * * * *